(12) United States Patent
Gabriel et al.

(10) Patent No.: US 8,900,517 B2
(45) Date of Patent: Dec. 2, 2014

(54) MODIFICATION OF SELECTIVITY FOR SENSING FOR NANOSTRUCTURE SENSING DEVICE ARRAYS

(75) Inventors: Jean-Christophe P. Gabriel, Quaix en Chartreuse (FR); Philip G. Collins, Oakland, CA (US); George Gruner, Los Angeles, CA (US); Keith Bradley, New York, NY (US)

(73) Assignee: Nanomix, Inc., Emeryville, CA (US)

( * ) Notice: Subject to any disclaimer, the term of this patent is extended or adjusted under 35 U.S.C. 154(b) by 1027 days.

(21) Appl. No.: 11/938,180

(22) Filed: Nov. 9, 2007

(65) Prior Publication Data
US 2011/0003698 A1 Jan. 6, 2011

Related U.S. Application Data

(62) Division of application No. 10/099,664, filed on Mar. 15, 2002, now Pat. No. 7,312,095.

(51) Int. Cl.
*G01N 33/00* (2006.01)
*G01N 27/414* (2006.01)
*G01N 35/00* (2006.01)

(52) U.S. Cl.
CPC .. *G01N 27/4146* (2013.01); *G01N 2035/00158* (2013.01); *Y10S 977/70* (2013.01); *Y10S 977/701* (2013.01); *Y10S 977/92* (2013.01); *Y10S 977/953* (2013.01); *Y10S 977/902* (2013.01); *Y10S 977/84* (2013.01); *Y10S 977/883* (2013.01); *Y10S 977/882* (2013.01); *Y10S 977/957* (2013.01)
USPC ........... 422/98; 422/50; 422/68.1; 422/82.01; 436/43; 436/149; 438/49; 438/21; 438/48; 977/700; 977/701; 977/957; 977/953; 977/920; 977/700; 977/902; 977/840; 977/883; 977/882

(58) Field of Classification Search
USPC ........... 422/50, 68.1, 82.01, 82.02, 82.03, 83, 422/98; 436/43, 149; 438/49, 21, 48; 977/700, 701, 840, 882, 883, 902, 920, 977/953, 957
See application file for complete search history.

(56) References Cited

U.S. PATENT DOCUMENTS
4,851,195 A 7/1989 Matthews et al.
4,935,345 A 6/1990 Guilbeau et al.
(Continued)

FOREIGN PATENT DOCUMENTS
WO 02/15240 2/2002
WO 2008/045799 4/2008
WO 2009/017911 2/2009

OTHER PUBLICATIONS
Ong et al., "A Carbon Nanotube-based Sensor for CO2 Monitoring," Sensors, vol. 1, pp. 193-205; published Nov. 2, 2001.*
(Continued)

*Primary Examiner* — Brian J Sines
(74) *Attorney, Agent, or Firm* — Weaver Austin Villeneuve & Sampson LLP

(57) ABSTRACT

An electronic system for selectively detecting and identifying a plurality of chemical species, which comprises an array of nanostructure sensing devices, is disclosed. Within the array, there are at least two different selectivities for sensing among the nanostructure sensing devices. Methods for fabricating the electronic system are also disclosed. The methods involve modifying nanostructures within the devices to have different selectivity for sensing chemical species. Modification can involve chemical, electrochemical, and self-limiting point defect reactions. Reactants for these reactions can be supplied using a bath method or a chemical jet method. Methods for using the arrays of nanostructure sensing devices to detect and identify a plurality of chemical species are also provided. The methods involve comparing signals from nanostructure sensing devices that have not been exposed to the chemical species of interest with signals from nanostructure sensing devices that have been exposed to the chemical species of interest.

12 Claims, 14 Drawing Sheets

(56) References Cited

U.S. PATENT DOCUMENTS

| | | | |
|---|---|---|---|
| 5,246,859 A | 9/1993 | Nelson et al. | |
| 5,382,417 A | 1/1995 | Haase | |
| 5,571,401 A * | 11/1996 | Lewis et al. | 205/787 |
| 5,736,188 A | 4/1998 | Alcock et al. | |
| 6,217,828 B1 | 4/2001 | Bretscher et al. | |
| 6,465,132 B1 | 10/2002 | Jin | |
| 6,489,394 B1 | 12/2002 | Andros | |
| 6,528,020 B1 * | 3/2003 | Dai et al. | 422/98 |
| 6,797,325 B2 | 9/2004 | Wang et al. | |
| 6,962,823 B2 | 11/2005 | Empedocles et al. | |
| 7,955,559 B2 | 6/2011 | Joshi et al. | |
| 8,425,745 B2 | 4/2013 | Briman et al. | |
| 2002/0117659 A1 | 8/2002 | Lieber et al. | |
| 2002/0130333 A1 | 9/2002 | Watanabe et al. | |
| 2003/0040173 A1 * | 2/2003 | Fonash et al. | 438/622 |
| 2003/0041438 A1 | 3/2003 | Wei et al. | |
| 2003/0077642 A1 | 4/2003 | Fritsch et al. | |
| 2003/0113713 A1 * | 6/2003 | Glezer et al. | 435/5 |
| 2003/0134433 A1 | 7/2003 | Gabriel et al. | |
| 2003/0186167 A1 * | 10/2003 | Johnson, Jr. et al. | 430/296 |
| 2004/0018587 A1 | 1/2004 | Makowski et al. | |
| 2004/0023428 A1 | 2/2004 | Gole et al. | |
| 2004/0065970 A1 | 4/2004 | Blanchet-Fincher | |
| 2004/0067646 A1 * | 4/2004 | Tao et al. | 438/689 |
| 2004/0091285 A1 | 5/2004 | Lewis | |
| 2004/0120183 A1 | 6/2004 | Appenzeller et al. | |
| 2004/0146958 A1 | 7/2004 | Bae et al. | |
| 2004/0158410 A1 | 8/2004 | Ono et al. | |
| 2004/0200734 A1 | 10/2004 | Co et al. | |
| 2004/0259180 A1 | 12/2004 | Burke et al. | |
| 2005/0186333 A1 | 8/2005 | Douglas | |
| 2005/0230270 A1 | 10/2005 | Ren et al. | |
| 2006/0040381 A1 | 2/2006 | Zhao et al. | |
| 2006/0115640 A1 | 6/2006 | Yodh et al. | |
| 2006/0141469 A1 | 6/2006 | Rossier et al. | |
| 2007/0208243 A1 | 9/2007 | Gabriel et al. | |
| 2008/0185295 A1 | 8/2008 | Briman et al. | |
| 2009/0084678 A1 | 4/2009 | Joshi et al. | |
| 2012/0018301 A1 | 1/2012 | Joshi et al. | |
| 2013/0306491 A1 | 11/2013 | Briman et al. | |

OTHER PUBLICATIONS

US Office Action dated Jun. 6, 2011 issued in U.S. Appl. No. 11/868,373.

US Final Office Action dated Feb. 6, 2012 issued in U.S. Appl. No. 11/868,373.

US Notice of Allowance dated Aug. 31, 2012 issued in U.S. Appl. No. 11/868,373.

US Notice of Allowance dated Dec. 21, 2012 issued in U.S. Appl. No. 11/868,373.

US Office Action dated Jun. 16, 2014 issued in U.S. Appl. No. 13/867,925.

US Office Action dated Feb. 25, 2008 issued in U.S. Appl. No. 11/274,747.

US Office Action Final dated Feb. 11, 2009 issued in U.S. Appl. No. 11/274,747.

US Office Action dated May 28, 2010 issued in U.S. Appl. No. 12/146,320.

US Notice of Allowance dated Dec. 3, 2010 issued in U.S. Appl. No. 12/146,320.

US Notice of Allowance dated Jan. 25, 2011 issued in U.S. Appl. No. 12/146,320.

US Office Action dated Jan. 25, 2013 issued in U.S. Appl. No. 13/092,869.

US Final Office Action dated Aug. 8, 2013 issued in U.S. Appl. No. 13/092,869.

US Notice of Allowance dated Dec. 10, 2013 issued in U.S. Appl. No. 13/092,869.

PCT International Search Report dated Sep. 9, 2008 issued in PCT/US07/080603.

PCT International Preliminary Report on Patentability and Written Opinion dated Apr. 7, 2009 issued in PCT/US07/080603.

PCT International Search Report dated Jan. 2, 2009 issued in PCT/US2008/68228.

PCT International Preliminary Report on Patentability and Written Opinion dated Jan. 5, 2010 issued in PCT/US2008/68228.

Zhao et al., (Jan. 2004) "Synthesis and Properties of a Water-Soluble Single-Walled Carbon Nanotube-Poly($m$-aminobenzene sulfonic acid) Graft Copolymer", *Adv. Funct. Mater.* 14(1):71-76.

* cited by examiner

MODIFICATION OF SELECTIVITY FOR SENSING FOR NANOSTRUCTURE SENSING DEVICE ARRAYS

CROSS REFRENCE TO RELATED APPLICATIONS

The present application is a divisional of and claims priority to co-pending U.S. patent application Ser. No. 10/099,664, filed Mar. 15, 2002, entitled "MODIFICATION OF SELECTIVITY FOR SENSING FOR NANOSTRUCTURE SENSING DEVICE ARRAYS", by inventors Gabriel et al., which is incorporated herein by reference in its entirety.

BACKGROUND OF THE INVENTION

1. Field of the Invention

This invention relates generally to a system for detecting and identifying chemical species and, more particularly, to a system that uses an array of nanostructure sensing devices, which have been modified for selectivity for sensing a plurality of chemical species and methods of fabricating the same.

2. Description of the Related Art

Chemical and biological sensing is important in many industrial, medical, agricultural, and environmental monitoring applications. Many industrial processes are monitored and kept within control limits by chemical sensing. Medical analyte sensors can determine levels of various chemicals in blood and other body fluids. There is a need to monitor environmental hazards, such as pollutants and biotoxins. Increasingly, there is a demand for chemical sensing with military application, such as detection of harmful chemical and biological agents and for treaty verification. Other applications include sensing simple odors, such as for foodstuffs (e.g., to determine freshness, grade quality, and maturity of cheeses and to identify flavors,), drinks (e.g., to classify wines, beers, whiskies and to analyze flavors as for coffee), perfumes and essential oils.

Some chemical sensors rely on solid state materials, such as semiconducting metal oxides. For example, a metal oxide semiconductor sensor has been described by Taguchi in U.S. Pat. No. 3,676,820. The electrical resistance of the metal oxide semiconductor sensor changes when chemical species are absorbed onto the sensor. These sensors operate best at high temperatures in order to achieve enhanced chemical reactivity between chemical species and sensor materials for significant sensitivity. Solid state sensors have long recovery times, poor reproducibility, and can detect only a limited variety of chemical species. Solid state sensors are limited by their lack of sensitivity to certain chemical species and by their non-linear response.

Other chemical detectors for detecting at the molecular level rely on polymer coated surface acoustic wave (SAW) sensors to detect and identify chemical species. A SAW sensor array has been described by Bowers et al. in U.S. Pat. No. 6,321,588. A SAW sensor operates in effect as a microbalance through the de-tuning of the crystal's resonant frequency as mass is added to its surface. When a SAW sensor is used as part of an oscillator, changes in the characteristics of acoustic waves propagating through the SAW sensor can be used to determine the nature of one or more substances that has adsorbed onto the sensor. The signal transduction mechanism involves somewhat complicated electronics, requiring frequency measurement to 1 Hz while sustaining a 100 MHz Rayleigh wave in the crystal.

There are chemical detectors for detecting gases and vapors that have been developed, which use gas chromatography. This method offers extremely good selectivity in separating chemical compounds. However, the gas chromatographic approach requires a significant amount of time for all chemical species to be detected, as they must be detected serially, which is very time-consuming. Furthermore, systems of this type are not small enough for many field applications.

Accordingly, there is a need for robust, sensitive and accurate sensors capable of detecting a wide variety of chemical species that utilize a simple electronic detection principle, can be used for a wide range of applications, can be manufactured easily and have the flexibility to expand their scope as new detection needs arise.

SUMMARY OF THE INVENTION

In accordance with one embodiment of the present invention, an electronic system for selectively detecting and identifying a plurality of chemical species, which comprises an array of nanostructure sensing devices, is provided. Each nanostructure sensing device comprises at least one nanostructure that has a selectivity for sensing chemical species. Within the array, the selectivity of at least one nanostructure sensing device differs from the selectivity of at least one other nanostructure sensing device. The nanostructure sensing devices can include gate electrodes positioned to influence conductivity in the nano structures.

In accordance with another embodiment of the invention, a method of fabricating an electronic system, comprising an array of nanostructure sensing devices, for selectively detecting and identifying a predetermined number of chemical species is provided. Each nanostructure sensing device in the array comprises at least one nanostructure and at least two contact electrodes. The at least one nanostructure provides electrical coupling between the contact electrodes. Selectivity for sensing of the nanostructures is modified within at least a portion of the array so that at least one nanostructure sensing device produces a measurably changed signal when exposed to the chemical species. Additional portions of the array undergo other modifications until each of the predetermined number of chemical species produces a measurably changed signal from the array of nanostructure sensing devices. Modification can involve using a reactant. The reactant can be a gas, a chemical solution, or an electrochemical solution. The measurably changed signal can be an electrical signal, an optical signal, a mechanical signal or a thermal signal.

In accordance with one aspect of the invention, a variety of reactants can be supplied to the nanostructure sensing devices in the array by a plurality of chemical jets. The nanostructure sensing devices can be modified for selectivity for sensing through a variety of reactions with a variety of reactants. The variety of reactions and reactants can supply a variety of selectivity for sensing within the array of nanostructure sensing devices such that each of the predetermined number of chemical species produces a measurably changed signal from the array.

In accordance with another aspect of the invention, the reactant is an electrochemical solution, and at least a portion of the array of nanostructure sensing devices is submerged in the reactant. A first voltage is applied to the contact electrodes in at least the portion of the array, and a second voltage, different from the first voltage, is applied to counter electrodes, thus effecting an electrochemical reaction between the electrochemical solution and the nanostructures within at least the portion of the array of nanostructure sensing devices. The electrochemical reaction is repeated, using different electrochemical solutions each time, until there is a variety of selectivity for sensing within the array of nanostructure sensing devices such that each of the predetermined number of chemical species produces a measurably changed signal from the array.

According to another aspect of the invention, nanostructure sensing devices, supplied with reactants, can be modified by applying a characteristic voltage across the contact electrodes. Initially, there is a current flow through the nanostructures. The characteristic voltage continues to be applied until the current flow decreases sharply, thereby introducing point defects into the nanostructures in a self-limiting reaction. The point defects themselves can have selectivity for sensing, or they can serve as attachment sites for further reactions with other molecules, which can have selectivity for sensing.

In accordance with another embodiment of the invention, methods for detecting a plurality of chemical species in a surrounding environment are provided. In one arrangement, first signals are measured from nanostructure sensing devices in an array before exposing the array to a surrounding environment. Second signals are measured from nanostructure sensing devices in the array after exposing the array to the surrounding environment. The signals can be measured while the nanostructures are under the influence of a gate voltage. A series of first and second signals can be made as a function of a series of gate voltages. A significant change between the first signals and the second signals from the array of nanostructure sensing devices indicates detection of a chemical species. Correlations are made between known signal changes that occur when known chemical species are detected and observed changes between the first signals and the second signals.

In another arrangement, an array of sets of nanostructure sensing devices is provided, each set comprising at least two nanostructure sensing devices that have the same selectivity for sensing. Within each set, at least one device is shielded to be impermeable to at least the plurality of chemical species of interest, and at least one device is at least partially exposed to at least the plurality of chemical species. Signals from the devices in each set are measured and compared after positioning the array in the environment of interest. Correlations are made between known signal differences for shielded and at least partially exposed nanostructure sensing devices when known chemical species are detected and observed differences in signals for shielded nanostructure sensing devices and at least partially exposed nanostructure sensing devices in the array of sets. Again, gate voltages or a series of gate voltages can be employed while making the measurements. The signals can be electrical signals, optical signals, mechanical signals, or thermal signals.

Further features and advantages of the present invention will become apparent to those of ordinary skill in the art in view of the detailed description of preferred embodiments below, when considered together with the attached drawings and claims.

BRIEF DESCRIPTION OF THE DRAWINGS

The figures are not drawn to scale.

DETAILED DESCRIPTION OF THE PREFERRED EMBODIMENT

Recently, nanostructures have attracted attention as sensor components. Coating of nanotubes to make nanostructure sensing devices has been described by Zhang et al. in Chemical Physics Letters 331 (2000), p. 35 and by Zhang et al. in Applied Physics Letters 77 (2000), p. 3015, which is included herein by reference. Nanostructure sensing devices show great promise for many applications. They can be made very small; even an array with a large number of nanostructure sensing devices can be made very small. They can be modified to detect a wide variety of chemical species. They use very little power. But in general, nanostructure sensing devices have been made only in small quantities for lab testing, and the techniques for producing nanostructure sensing devices have not been developed for large-scale manufacturing.

The preferred embodiments of the present invention are illustrated in the context of using an array of nanostructure sensing devices to detect a plurality of chemical species. The skilled artisan will readily appreciate, however, that the materials and methods disclosed herein will have application in a number of contexts where sensing of multiple chemical species is desired.

These and other objects and advantages of the present invention will become more fully apparent from the following description taken in conjunction with the accompanying figures. Reference will now be made to the figures wherein like numerals refer to like parts throughout.

Figure 1:
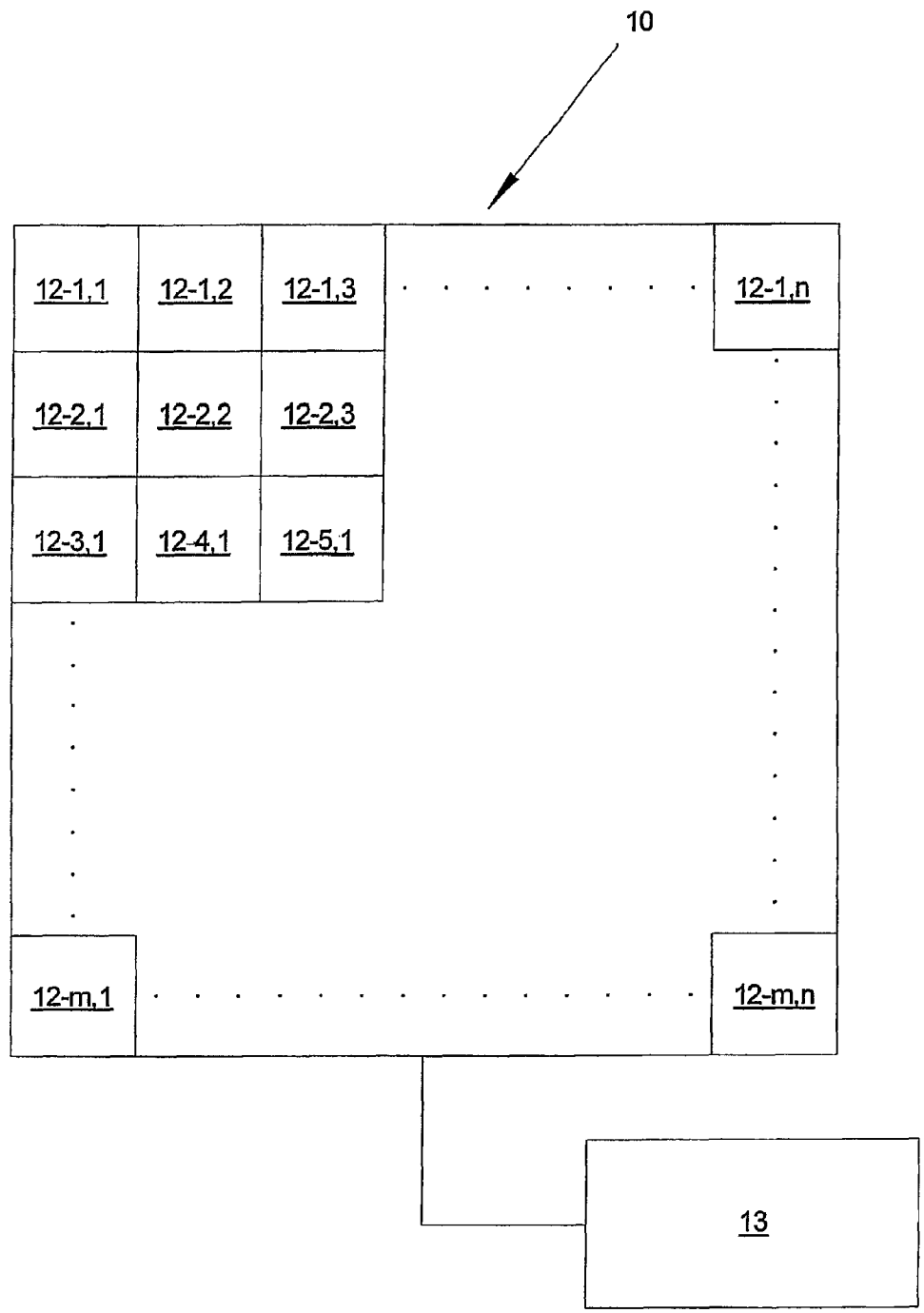
FIG. 1 is a schematic drawing of an electronic system for selectively detecting and identifying a plurality of chemical species.

FIG. 1 is a schematic illustration of an electronic system for selectively detecting and identifying a plurality of chemical species. The system includes an array 10 of nanostructure sensing devices 12-a,b, wherein, for the purpose of this illustration, a designates the row number, and b designates the column number of each device up to a maximum of m rows and n columns, where a, b, m, n are all integers. Each nanostructure sensing device 12-a,b has at least one nanostructure, and the at least one nanostructure in each device 12-a,b has a particular selectivity for sensing chemical species. The chemical species can be detected in either liquid or gaseous form. Selectivity for sensing is used here to mean that the nanostructure responds selectively to a chemical species in a way that produces a measurably changed and reproducible signal in the nanostructure sensing device. A measurably changed signal means that a signal produced by the nanostructure sensing device before exposure to the chemical species of interest is measurably different from a signal produced by the same nanostructure sensing device after exposure to the chemical species of interest. Signals can include electrical, optical, mechanical and thermal signals. The selectivity for sensing for each nanostructure sensing device is different from at least one other nanostructure sensing device in the array.

In other arrangements, there is a wide variety of selectivity for sensing among the nanostructure sensing devices in the array, so that a large number of chemical species can be detected. Total selectivity, that is, complete selectivity of a chemical species by a single nanostructure sensing device, may not be obtained, but the responses of individual nanostructure sensing devices are reproducible, and their resulting signals are well-characterized. These signals can be analyzed to identify the chemical species detected. Any chemical species can be identified as long as it generates a unique and differential response across a plurality of sensors in the array.

The measurably changed signals of the nanostructure sensing devices indicate the presence of chemical species. Measurable signals can include electrical signals, optical signals, mechanical signals and thermal signals. The set of changes in signal from the nanostructure sensing devices provides a basis for interpretation and analysis to identify chemical species which are present. The set of signal changes can be relayed to a processing system 13 (FIG. 1), where interpretation and analysis can be performed to provide identification of chemical species.

Figure 2:
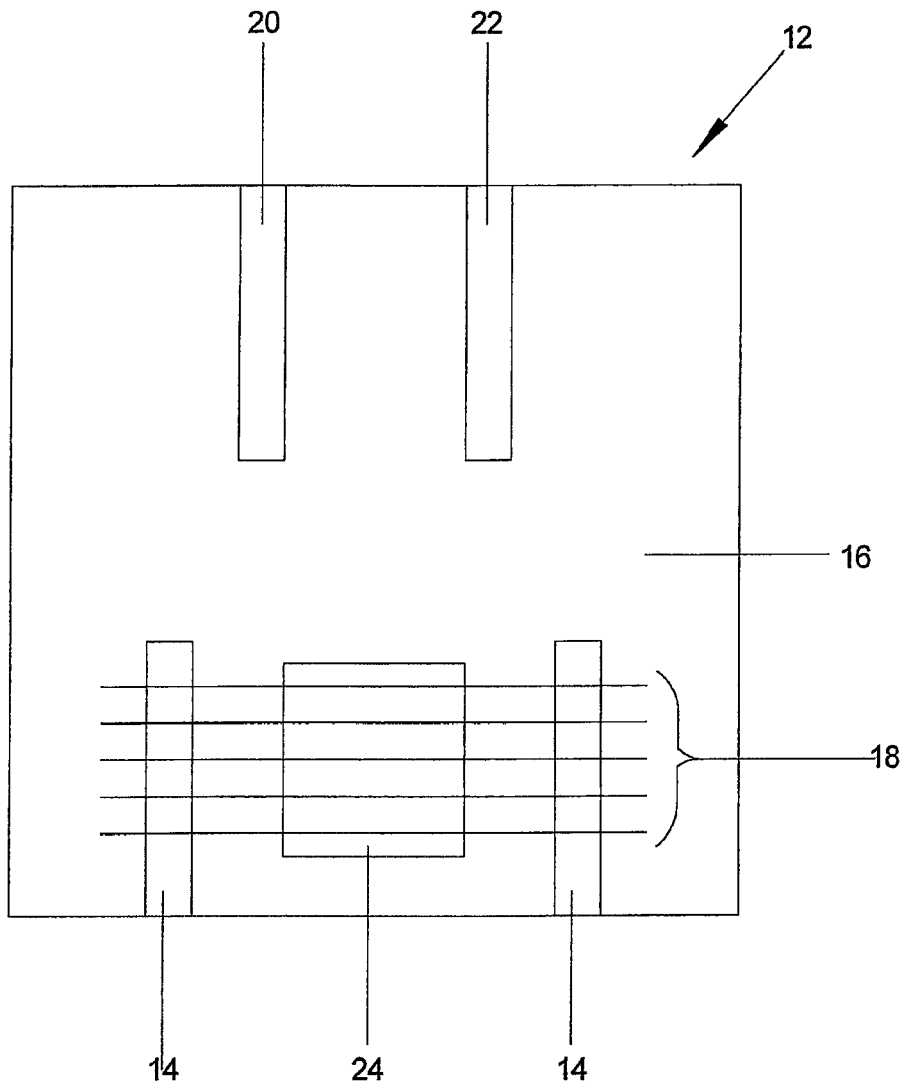
FIG. 2 shows an individual nanostructure sensing device according to an embodiment of the invention.

FIG. 2 is a schematic illustration of a single nanostructure sensing device 12 according to an embodiment of the invention. The nanostructure sensing device 12 has two contact electrodes 14 lying over a substrate 16, but any number of contact electrodes 14 can be used. The substrate 16 can be a semiconductor material and can be overlaid by an insulating layer as is known in the art of semiconductor manufacturing. The electrodes 14 are conducting elements made of any conducting material consistent with semiconductor manufacturing. Examples include aluminum, copper, titanium and tungsten. Nanostructures 18 are in electrical contact with the contact electrodes 14 and extend along the space between the contact electrodes 14. In some arrangements, the nanostructures 18 are pre-formed and then applied across the contact electrodes 14. In other arrangements, the nanostructures 18 are grown in place over the substrate 16 in a way that brings the nanostructures 18 into contact with the contact electrodes 14. In some arrangements, the nanostructures 18 are in contact with the substrate 16 between the contact electrodes 14. In other arrangements, the nanostructures 18 are suspended above the substrate 16 with an intervening space between the nanostructures 18 and the substrate 16. In some arrangements (not shown), there is a protective coating on the contact electrodes. In some arrangements, the protective coating covers portions of the nanostructures 18, preferably the portions where the nanostructures 18 are in contact with the contact electrodes 14. Materials that can be used for the protective coating include silicon oxides, metal oxides, polymer films, and nonvolatile organics.

The nanostructures 18 include forms such as single-walled nanotubes, multi-walled nanotubes, nanofibers, nanowires, nanocoils, nanospheres, nanocages, nanococoons, nanohorns, nanoropes, nanotori, nanorods, nanoplatelets, and other large, extended macromolecules such as polymers, dendrimers, organometallics, and fullerene-like molecules. The nanostructures 18 can include one or several forms. The nanostructures 18 can be turbostratic, highly oriented, twisted, straight, curled and rigid. The nanostructures 18 can have zig-zag chirality, or a mixture of chiralities. Nanostructures 18 can be twisted, straight, bent, kinked, curled, flattened, or round. Nanostructures 18 having an approximately linear form can be arranged in bundles of structures, such as ropes, braids or twisted bundles. The nanostructures 18 can be empty, filled, and multifaceted. The nanostructures 18 can be made of any element known to form nanostructures, for example, carbon, boron, carbon nitride, boron nitride, or carbon boron nitride. The chemical composition of a nanostructure 18 can be homogeneous or can vary throughout the structure. The nanostructures 18 can have cracks, dislocations, branches or other imperfections.

Preferably, the nanostructures 18, as used in the embodiments disclosed herein, have approximately linear forms, i.e., forms that can extend to make contact with electrodes 14. An approximately linear form can be achieved by using nanostructures that have an approximately linear form naturally, such as nanotubes, nanofibers, nanowires, nanoropes and nanorods. Alternatively, nanostructures having other forms, such as nanospheres, nanocages, nanococoons and nanotori, can be combined with one another or with other nanostructures to create an overall approximately linear form. Within an array of nanostructure sensing devices, the nanostructures can vary from nanostructure sensing device to nanostructure sensing device.

In FIG. 2 and according to another aspect of the invention, the nanostructure sensing device 12 can include a counter electrode 20. The nanostructure sensing device 12 can also include a pseudo-reference electrode 22. The counter electrode 20 and pseudo-reference electrode 22 can be used in an electrochemical reaction to modify selectivity for sensing of the nanostructures 18, as will be explained later. Materials commonly used for counter electrodes 20 and pseudo-reference electrodes 22 include graphite and metals.

In other arrangements and also shown in FIG. 2, the nanostructure sensing device 12 can include a gate electrode 24 positioned to influence conductivity in the nanostructures 18.

Figure 3:
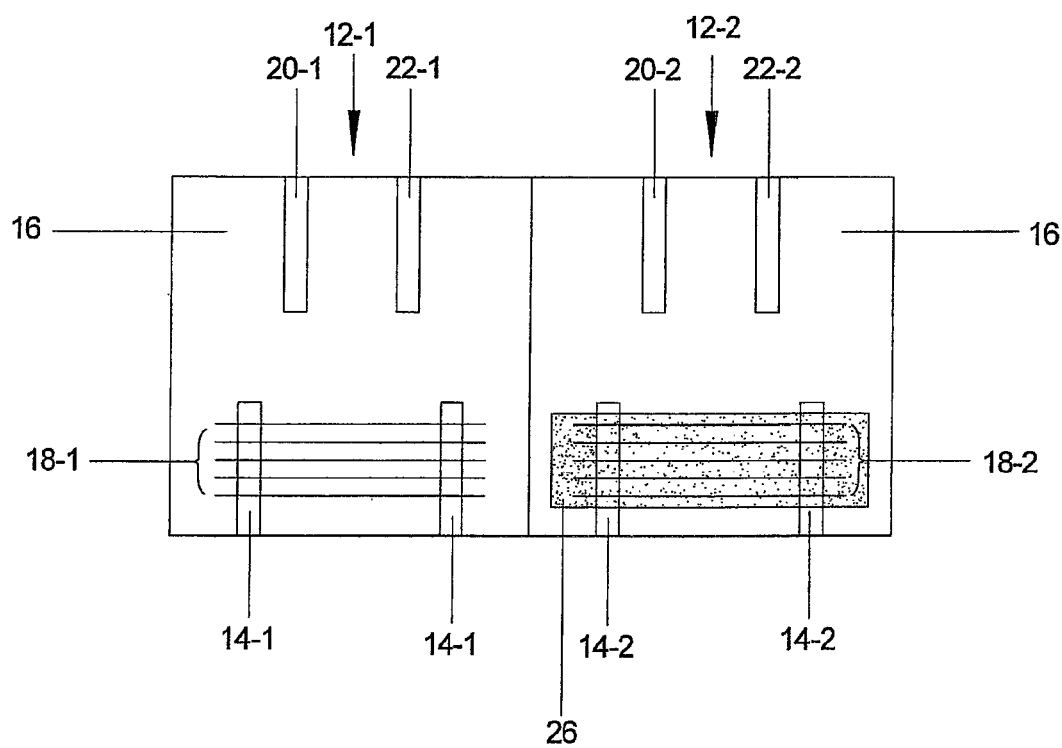
FIG. 3 shows a pair of nanostructure sensing devices having the same selectivity for sensing chemical species. The nanostructures in one of the nanostructure sensing devices are at least partially shielded from the environment, and the nanostructures in the other nanostructure sensing device are at least partially exposed to the environment, according to an embodiment of the invention.

FIG. 3 shows schematically a pair of nanostructure sensing devices 12-1, 12-2 whose nanostructures 18-1, 18-2 have been modified to have the same selectivity for sensing. Each of the illustrated nanostructure sensing devices has a pair of contact electrodes 14-1, 14-2, a substrate 16, a number of nanostructures 18-1, 18-2 having an approximately linear form, a counter electrode 20-1, 20-2, and a pseudo-reference electrode 22-1, 22-2, as have been discussed above in reference to FIG. 2. The nanostructures 18-1 in nanostructure sensing device 12-1 can be fully exposed to a surrounding environment, as shown in FIG. 2. In other arrangements, the nanostructures 18-1 can be partially shielded by permeable or selectively permeable membranes so that nanostructures 18-1 are at least partially exposed to the species of interest in the surrounding environment. As shown in FIG. 3, the nanostructures 18-2 in nanostructure sensing device 12-2 are covered by a shield 26 that can be completely impermeable to the surrounding environment. In other arrangements, the shield 26 can be impermeable to at least the species of interest, but still provide less exposure to the surrounding environment than any partial shield on nanostructures 18-1.

The arrangement shown in FIG. 3 can be extended to a whole array of nanostructure sensing devices. Within the array, there can be a plurality of sets of nanostructure sensing devices wherein the devices within any one set all have the same selectivity for sensing. In addition, within any one set, the nanostructures in some nanostructure sensing devices are shielded from at least the species of interest and the nanostructures in other nanostructure sensing devices are at least partially exposed to the species of interest in the surrounding environment, as has been described above for the two nanostructure sensing devices 12-1, 12-2 in FIG. 3. The selectivity for sensing for devices in one set is different from the selectivity for sensing for devices in another set.

Figure 4:
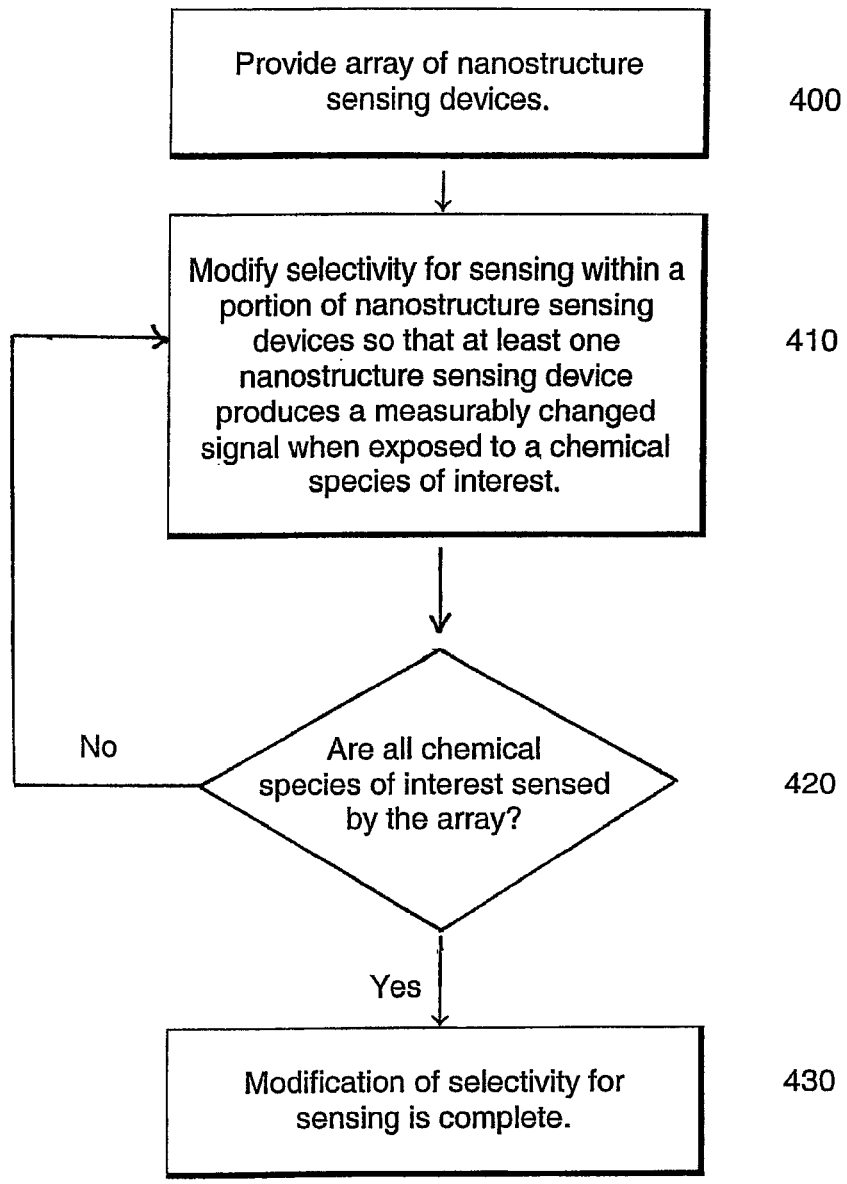
FIG. 4 is a flow chart showing a method of fabricating an electronic system for selectively detecting and identifying a predetermined number of chemical species according to an embodiment of the invention.

FIG. 4 shows a flow chart that summarizes the steps of a method of fabricating an electronic system for selectively detecting and identifying a predetermined number of chemical species of interest. Step 400 involves providing an array of nanostructure sensing devices. Each nanostructure sensing device includes at least one nanostructure that is connected electrically to at least two contact electrodes. In Step 410, selectivity for sensing within a portion of nanostructure sensing devices is modified so that at least one nanostructure sensing device produces a measurably changed signal when exposed to the chemical species of interest. A measurably changed signal means that a signal produced by the nanostructure sensing device before exposure to the chemical species of interest is measurably different from a signal produced by the same nanostructure sensing device after exposure to the chemical species of interest. Signals can include electrical, optical, mechanical and thermal signals. Modifying can involve using a reactant, either a liquid or a gas. The reactant can be a chemical solution or an electrochemical solution. Additional energy for the modification can be supplied by ultraviolet, thermal, or electrical energy. In some arrangements, before Step 410, the contact electrodes can be coated with a material that is impervious to the reactant. In some arrangements, before Step 410, portions of the nanostructures can be coated with a material that is impervious to the reactant. For example, materials such as silicon oxides, metal oxides, polymer films, and nonvolatile organics can be used for the coatings. Step 420 involves deciding whether all of the predetermined number of chemical species, i.e., the species of interest, are sensed by the array. If not all chemical species are sensed, Step 410 is perfomed on another portion of the array so that at least one nanostructure sensing device produces a measurable signal when exposed to at least one of the chemical species that had been found not to be sensed previously in Step 420. The decision of Step 420 is made again. As long as there are chemical species of interest that are not sensed by the array, Step 410 and decision Step 420 continue to be performed. When the decision at Step 420 is that all chemical species of interest are sensed by the array of nanostructure sensing devices, the method moves on to Step 430, wherein modification of selectivity for sensing is complete.

Nanostructures are modified to change the way they respond to chemical species of interest. There are a number of ways in which the modification can be effected. In one example, a material can be deposited (such as by chemical or electrochemical means) onto a nanostructure in a continuous coating. The continuous coating can be highly absorbent for or reactive with a chemical species of interest, but, in any case, the coating interacts strongly with the chemical species of interest, and thus produces a response, such as an electrical, thermal or optical signal. The underlying nanostructure can act essentially as a substrate for the coating.

In another example, the deposited coating is not continuous, but the coating still responds strongly to a chemical species of interest. The response can be communicated to the nanostructure through a variety of means, such as charge transfer, electric dipoles, thermally, or by mechanical strain. The nanostructure can act as a transducer for the response signal.

In yet another example, a deposited coating is not an element of the modification of the nanostructure. A reactant and a nanostructure engage in a reaction, such as a chemical or an electrochemical reaction, which results in a point defect in the nanostructure. As used herein, a point defect is defined to be a site on the nanostructure where the normal arrangement, that is, the arrangement before modification, of chemical bonds is disrupted. This can be a single broken bond, or it can be a small number of missing or rearranged atoms. The point defect can be defined further by its functionality. The point defect is an atomic site or cluster of atomic sites where the chemical nature and reactivity are different from the bulk of the nanostructure. Point defects can have selectivity for sensing. Point defects can also serve as attachment sites for further reactions as will be discussed below with reference to FIG. 8. Molecules in the reactant and atoms within the nanostructure whose bonds have been disrupted can bond to form other kinds of point defects. The nanostructure can act as both detector of the chemical species and transducer of the response signal.

Chemical jet technology, similar to inkjet technology, allows deposition of droplets of reactants of very small size at precise locations on a given surface. A chemical jet dispenser has been described by Swierkowski (U.S. Pat. No. 5,877,580), which is incorporated by reference herein. A set of reactant reservoirs containing different reactants and delivery channels can be used to deposit a large number of different reactants. Reactant droplet size can be adjusted so that the droplet covers only one nanostructure sensing device or so that one droplet extends over several devices.

Figure 5:
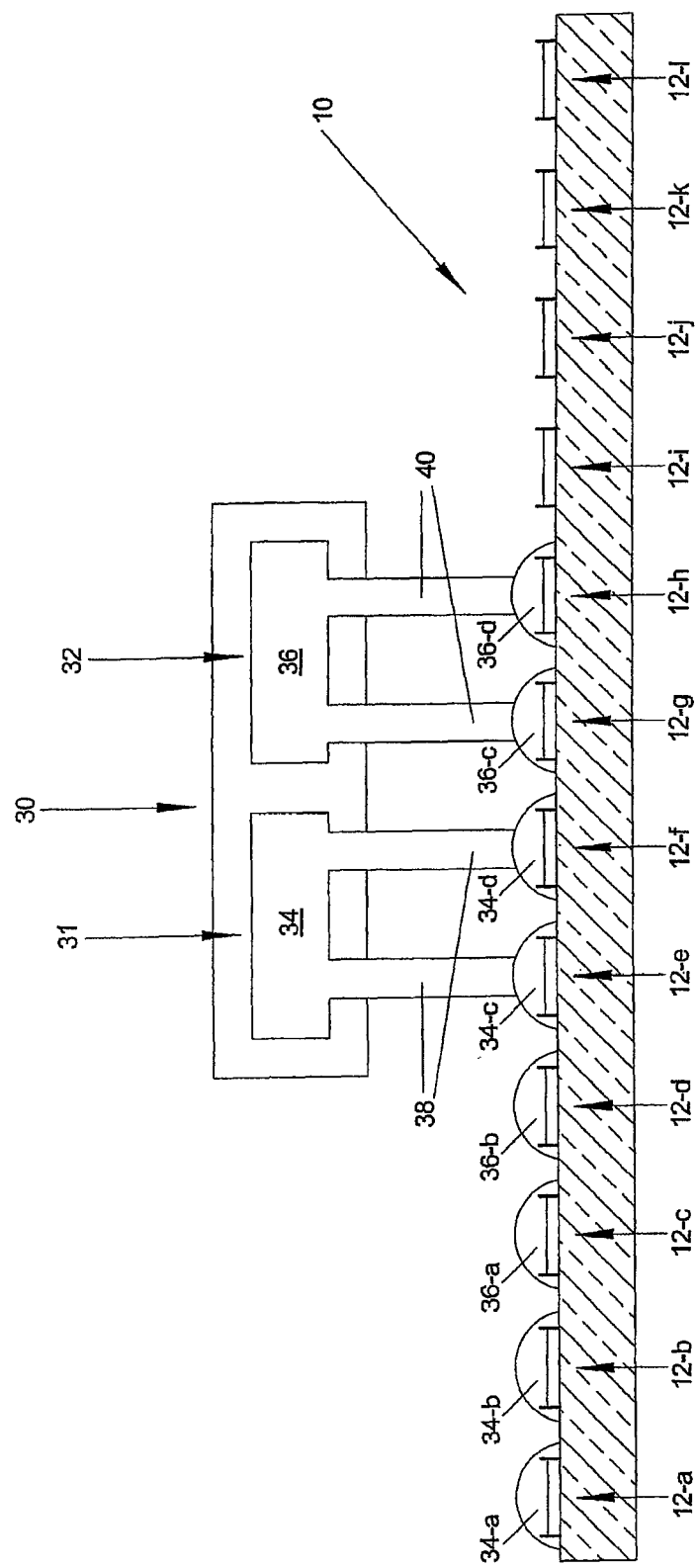
FIG. 5 is a cross-sectional view of chemical jets dispensing drops of reactant onto a portion of an array of nanostructure sensing devices.

FIG. 5 shows schematically a cross-sectional view of a chemical jet system 30 that dispenses drops of reactant onto nanostructure sensing devices 12-*a*-12-*l* on a portion of an array 10, according to an illustrated embodiment of the invention. FIG. 5 includes two reactant reservoirs 31, 32, each containing a reactant 34, 36, respectively. Reactants 34, 36 can be the same, or they can be different. Reactant 34 is dispensed through chemical jets 38, and reactant 36 is dispensed through chemical jets 40. The chemical jet system 30 has already dispensed reactant drops 34-*a*, 34-*b*, 36-*a*, 36-*b* onto nanostructure sensing devices 12-*a*, 12-*b*, 12-*c*, 12-*d*, respectively. It is preferred to expose each nanostructure sensing device only to the reactants that will interact with the nanostructures to achieve the desired modification. The chemical jet system 30 makes it possible to avoid cross-contamination or cross-reactivity between individual nanostructure sensing devices.

The chemical jet system 30 of FIG. 5 is positioned over the next set of four nanostructure sensing devices 12-*e*, 12-*f*, 12-*g*, 12-*h* in the portion of the array 10. Reactant 34 leaves reservoir 31 through chemical jets 38 to dispense drops 34-*c*, 34-*d* onto nanostructure sensing devices 12-*e*, 12-*f*, respectively. Similarly, reactant 36 leaves reservoir 32 through chemical jets 40 to dispense drops 36-c, 36-d onto nanostructure sensing devices 12-g, 12-h, respectively. In FIG. 5, the chemical jets 38, 40 are shown in contact with the reactant drops 34-c, 34-d, 36-c, 36-d. In some arrangements, the chemical jets 38, 40 can include counter electrodes (not shown) and pseudo-reference electrodes (not shown), which can be used to effect electrochemical reactions within the reactant drops 34-c, 34-d, 36-c, 36-d, as will be discussed in more detail with reference to FIG. 6 below.

After the drops 34-c, 34-d, 36-c, 36-d have been dispensed, and after electrochemical reactions that require contact between the chemical jets, such as 38, and reactant drops, such as 34-c, 34-d, have occurred, the chemical jet system 30 moves forward to align the chemical jets 38, 40 with the next four nanostructure sensing devices 12-i, 12-j, 12-k, 12-1 and to proceed with dispensing reactants 34, 36.

Although for purposes of illustration, FIG. 5 shows two reactant reservoirs 31, 32, four chemical jets 38, 40, and only a portion of a nanostructure sensing device array 10, the skilled artisan will understand readily that this system can include any number of reactant reservoirs and any number of chemical jets to be applied to any size nanostructure sensing device array. A wide variety of stepping patterns across the array can also be employed. Although FIG. 5 shows one drop of reactant for each nanostructure sensing device, it should be understood that in some arrangements, one reactant drop can cover a number of nanostructure sensing devices to modify the selectivity for sensing of the number of nanostructure sensing device in the same way.

Figure 6:
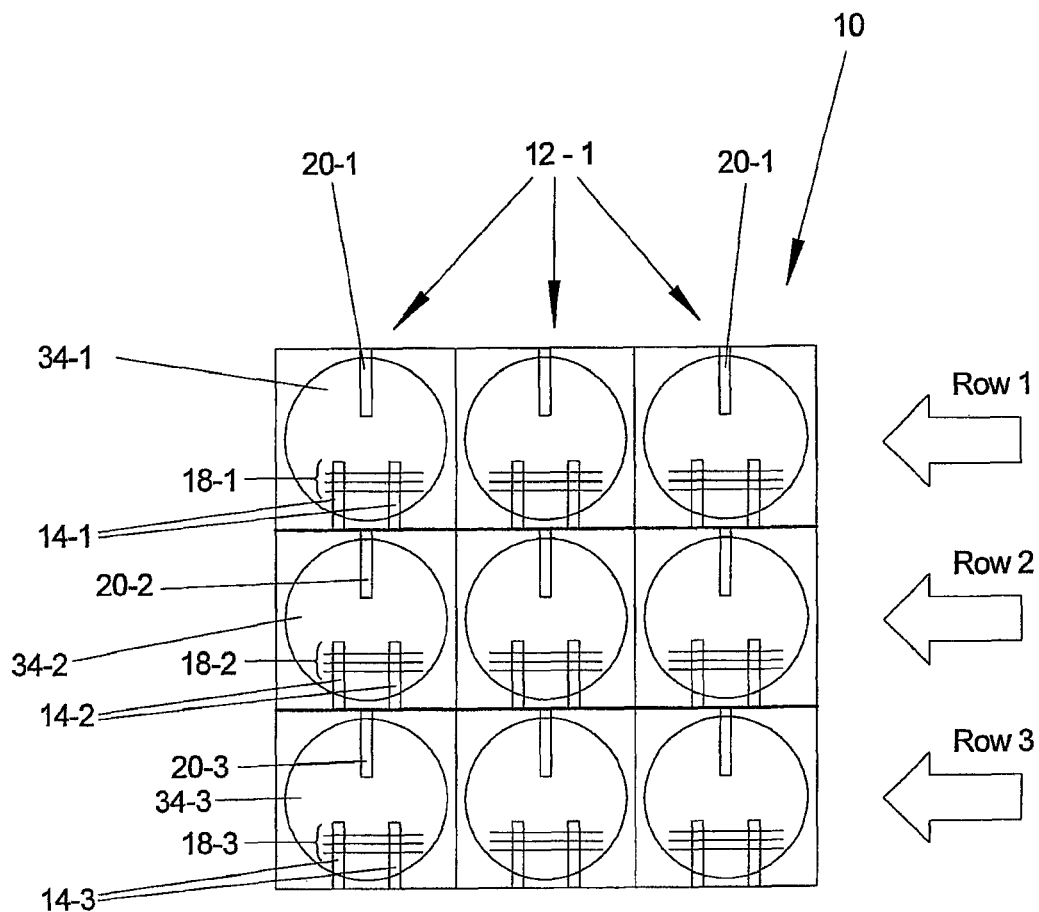
FIG. 6 is a top view of a portion of an array of nanostructure sensing devices onto which reactant drops have been dispensed.

FIG. 6 shows schematically an array 10 of nanostructure sensing devices 12. For the purpose of illustration, the array 10 contains only nine nanostructure sensing devices 12. Of course, in an actual array, there can be as many as $10^6$ or more nanostructure sensing devices, as is known in the art of semiconductor device manufacturing. In the illustrated embodiment, each nanostructure sensing device includes two contact electrodes 14-n, a number of nanostructures 18-n, and a counter electrode 20-n, wherein n is an integer indicating the row number in the array where the feature is located, all on a substrate 16. In other arrangements, each nanostructure sensing device can include also a pseudo-reference electrode (not shown). For the purpose of illustration, three rows 1, 2, 3 of nanostructure sensing devices are shown. Of course, there can be any number of rows of devices. The methods disclosed herein are not limited to modification of selectivity for sensing within rows of nanostructure sensing devices, but can apply to any portions of the array for which different selectivity for sensing is desired.

In row 1, drops of reactant 34-1 have been dispensed from a chemical jet onto each nanostructure sensing device 12-1. In row 2, drops of reactant 34-2 have been dispensed from a chemical jet onto each nanostructure sensing device 12-2. In row 3, drops of reactant 34-3 have been dispensed from a chemical jet onto each nanostructure sensing device 12-3. In this example, reactants 34-1, 34-2, 34-3 are all electrochemical solutions and each is different from the others. Electrochemical solutions are well known in the art. Possible solutions for modifying selectivity for sensing of nanostructures include those used for electroplating metals, for electro-induced polymerization and for electro-crystallization.

A first voltage is applied to contact electrodes 14-1, and a second voltage, different from the first voltage, is applied to counter electrodes 20-1, thus effecting an electrochemical reaction within the drops of reactant 34-1. Similarly for the nanostructure sensing devices in Row 2, a third voltage is applied to the contact electrodes 14-2 and a fourth voltage, different from the third voltage is applied to counter electrodes 20-2, thus effecting an electrochemical reaction within the drops of reactant 34-2. Again for the nanostructure sensing devices in Row 3, a fifth voltage is applied to the contact electrodes 14-3 and a sixth voltage, different from the fifth voltage is applied to counter electrodes 20-3, thus effecting an electrochemical reaction within the drops of reactant 34-3. The first, third and fifth voltages may or may not be the same. The second, fourth, and sixth voltages may or may not be the same. The electrochemical reactions cause modification of the selectivity for sensing of the nanostructures 18-1, 18-2, 18-3 within the array 10. A pseudo-reference electrode for helping to control the electrochemical reaction, as is known in the art, can be provided. The pseudo-reference electrode can be a component of the chemical jets, and voltages can be applied to effect electro-chemical reactions while the chemical jets are in contact with the drops of reactant. Alternatively, pseudo-reference electrodes can be provided as components of the nanostructure sensing devices, as illustrated in FIG. 2. The electrochemical reactions can be monitored and controlled by controlling the potential on the electrodes, the amount of current in the reactions, the concentration of the solution, or by time, as is known in the art. In an alternative arrangement, the nanostructure sensing devices do not include counter electrodes 20-n. Counter electrodes (not shown) are provided in the chemical jets, and the electrochemical reactions occur while the chemical jets are dispensing the drops 34-n of reactant.

Another embodiment of the invention can be understood with reference to FIG. 6. The array 10 of nanostructure sensing devices 12-1, 12-2, 12-3 is as shown in FIG. 6 except that there are no counter electrodes 20-1, 20-2, 20-3. The drops 34-1, 34-2, 34-3 of reactant react with the nanostructures 18-1, 18-2, 18-3, respectively, chemically, instead of electrochemically, to modify the selectivity for sensing of the nanostructures 18-1, 18-2, 18-3.

Another embodiment of the invention can be understood with reference to FIG. 6. Again, the array 10 of nanostructure sensing devices 12-1, 12-2, 12-3 is as shown in FIG. 6 except that there are no counter electrodes 20-1, 20-2, 20-3. The drops 34-1, 34-2, 34-3 of reactant are dispensed onto the nanostructure sensing devices 12-1, 12-2, 12-3. FIG. 6 illustrates an arrangement where each drop 34-1, 34-2, 34-3 of reactant is confined to only one nanostructure sensing device. In other arrangements, a drop of reactant 34 can extend over many nanostructure sensing devices. A voltage is applied across each pair of contact electrodes 14-1, 14-2, 14-3, and a current flows through the nanostructures 18-1, 18-2, 18-3, respectively. The voltage is increased gradually in each nanostructure sensing device 12-1, 12-2, 12-3, thereby gradually increasing current flow through the nanostructures. The increasing energy from the increasing current flow can lead to a reaction between the nanostructures and the reactant, which causes formation of one or more point defects. When a point defect forms, there is a large increase in resistance, there is a sharp decrease in current flow through the nanostructures, and the reaction stops. The characteristic voltage at which the reaction becomes, i.e., at which the reaction stops, can be different for each device. Point defects produced in the self-limiting reaction can have selectivity for sensing chemical species. Point defects can also serve as attachment sites for molecules in further reactions as will be discussed below. In subsequent processing to modify selectivity for sensing of nanostructure sensing devices, it is not necessary to apply an increasing voltage to form the point defects. The previously-found characteristic voltages can be applied for known periods of time until the point defects form and the reaction stops.

In any of the embodiments discussed above with reference to FIG. 6, the modification reaction can be initiated or controlled by supplying to the array additional forms of energy (not shown), such as ultraviolet radiation, thermal energy, or electrical energy.

Preferably, the chemical jet processes described above are performed in a controlled atmosphere to mitigate evaporation of the reactant droplets, as is known in the art.

Figure 7A:
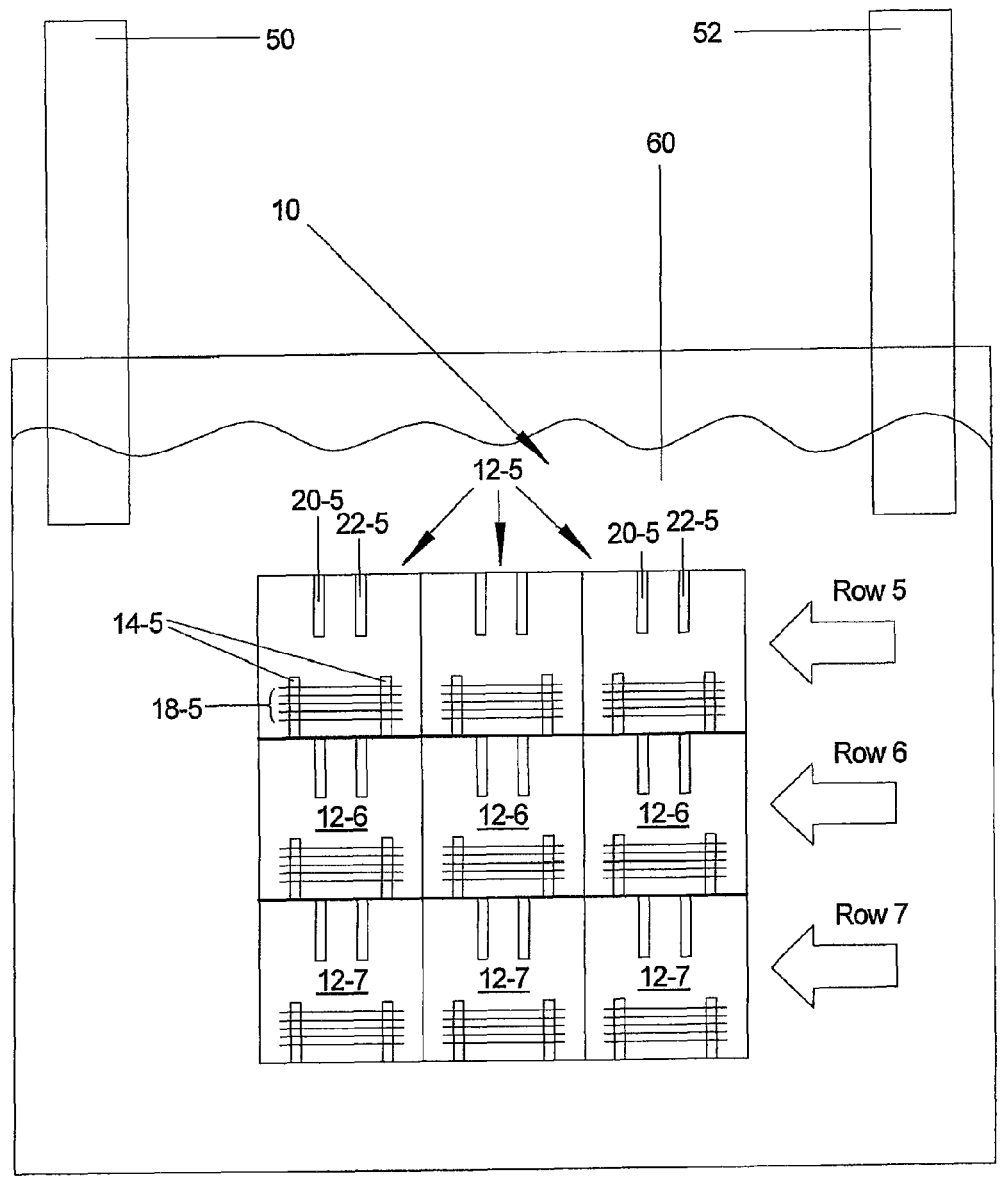
FIG. 7A is a view of a portion of an array of nanostructure sensing devices submerged in a first reactant.
Figure 7B:
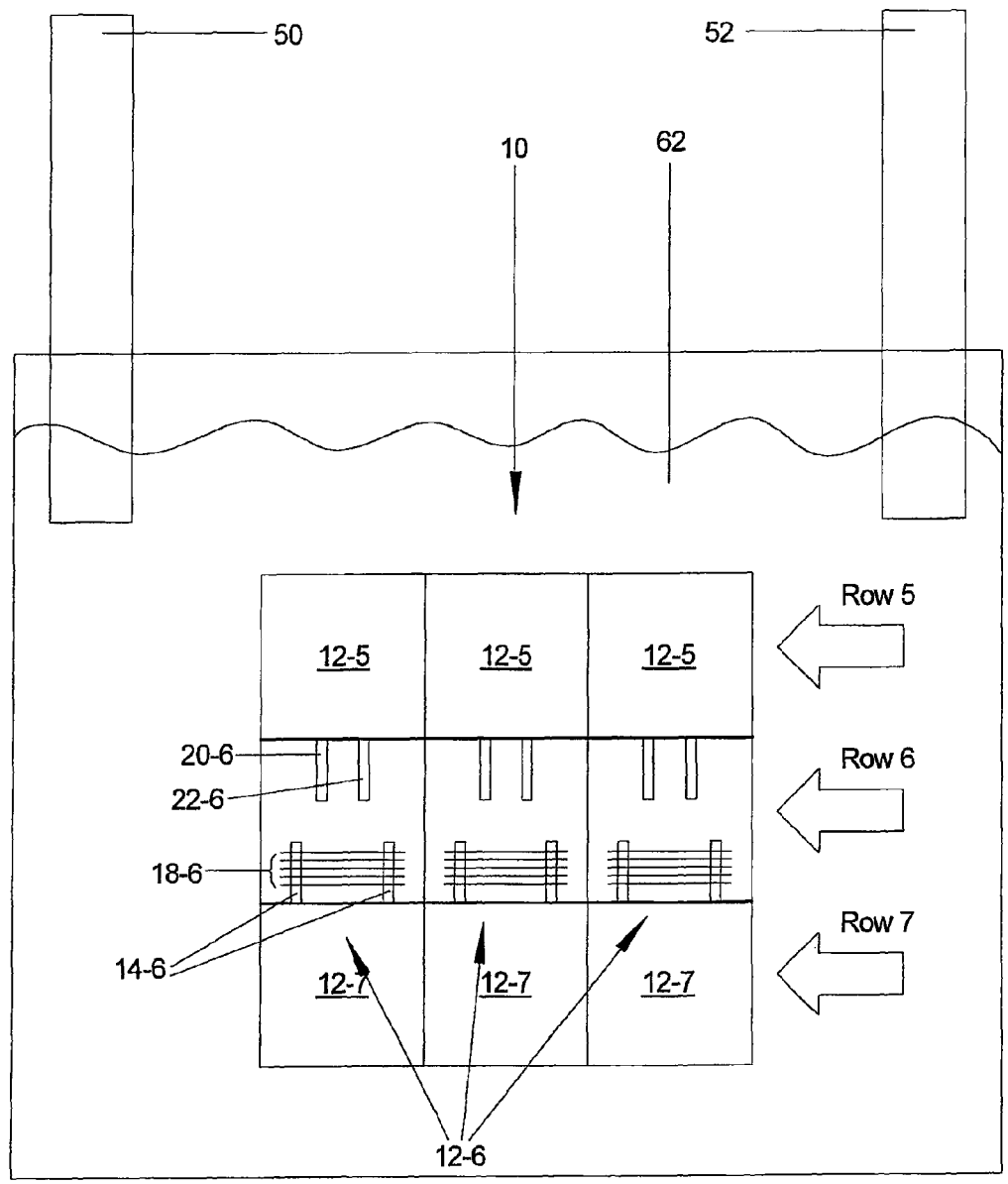
FIG. 7B is a view of a portion of an array of nanostructure sensing devices submerged in a second reactant.
Figure 7C:
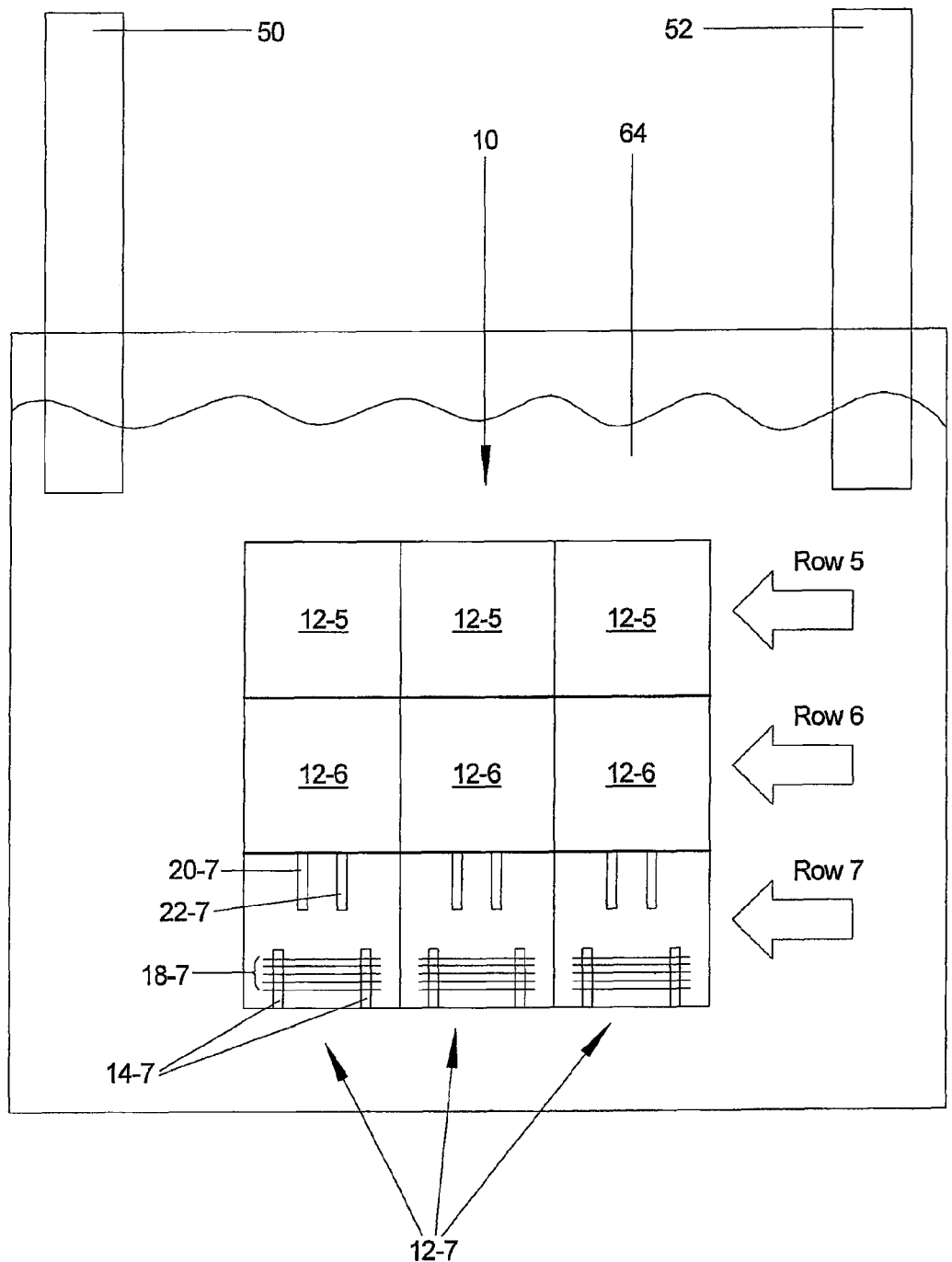
FIG. 7C is a view of a portion of an array of nanostructure sensing devices submerged in a third reactant.

FIG. 7A-7C are schematic drawings illustrating a method of making a system for selectively detecting and identifying a predetermined number of chemical species according to another embodiment of the invention. For the purpose of illustration, an array 10 containing only nine nanostructure sensing devices 12 is shown. Of course, in an actual array, there can be any number of nanostructure sensing devices, as in known in the art of semiconductor manufacturing. In the illustrated embodiment, each nanostructure sensing device 12-$n$ includes two contact electrodes 14-$n$, a number of nanostructures 18-$n$, and may also include a counter electrode 20-$n$ and a pseudo-reference electrode 22-$n$, wherein n is an integer indicating the row number in the array where the feature is located, all on a substrate 16. Each nanostructure sensing device 12 is electrically insulated on the substrate from the other nanostructure sensing devices. For the purpose of illustration, three rows 5, 6, 7 of nanostructure sensing devices are indicated. Of course, there can be any number of rows of devices. Furthermore, the methods disclosed herein are not limited to modification of selectivity for sensing within rows of nanostructure sensing devices, but can apply to any portions of the array for which different selectivity for sensing is desired.

In FIG. 7A, the entire array 10 has been submerged in a first reactant bath 60. Alternatively, only a portion of the array 10, for which modification of selectivity for sensing is desired, such as Row 5, can be submerged in the reactant bath 60. In the example illustrated in FIGS. 7A-7C, each nanostructure sensing device includes two contact electrodes 14-$n$, a number of nanostructures 18-$n$, and a counter electrode 20-$n$, wherein n is an integer indicating the row number in the array where the feature is located, all on a substrate 16. In other arrangements, each nanostructure sensing device can include also a pseudo-reference electrode (not shown). For the purpose of illustration, three rows 5, 6, 7 of nanostructure sensing devices are shown. Of course, there can be any number of rows of devices. The methods disclosed herein are not limited to modification of selectivity for sensing within rows of nanostructure sensing devices, but can apply to any portions of the array for which different selectivity for sensing is desired. In this example, reactant 60 contains an electrochemical solution. A first voltage is applied to contact electrodes 14-5, and a second voltage, different from the first voltage is applied to counter electrodes 20-5, thus effecting an electrochemical reaction between the electrochemical solution and the nanostructures 18-5 and causing modification of the selectivity for sensing of the nanostructures 18-5 within the array 10. After modification of nanostructures 18-5, the array 10 is removed from the reactant bath 60, and the array 10 is rinsed.

In FIG. 7B, the entire array 10 has been submerged in a second reactant bath 62. The details of structures on only row 6 are shown. Alternatively, only a portion of the array 10, for which modification of selectivity for sensing is desired, such as Row 6, can be submerged in the reactant bath 62. In this example, reactant 62 contains an electrochemical solution. A first voltage is applied to contact electrodes 14-6, and a second voltage, different from the first voltage is applied to counter electrodes 20-6, thus effecting an electrochemical reaction between the electrochemical solution and the nanostructures 18-6 and causing modification of the selectivity for sensing of the nanostructures 18-6 within the array 10. After modification of nanostructures 18-6, the array 10 is removed from the reactant bath 62, and the array 10 is rinsed.

In FIG. 7C, the entire array 10 has been submerged in a third reactant bath 64. The details of structures on only row 7 are shown. Alternatively, only a portion of the array 10, for which modification of selectivity for sensing is desired, such as Row 7, can be submerged in the reactant bath 64. In this example, reactant 64 contains an electrochemical solution. A first voltage is applied to contact electrodes 14-7, and a second voltage, different from the first voltage is applied to counter electrodes 20-7, thus effecting an electrochemical reaction between the electrochemical solution and the nanostructures 18-7 and causing modification of the selectivity for sensing of the nanostructures 18-7 within the array 10. After modification of nanostructures 18-7, the array 10 is removed from the reactant bath 64, and the array 10 is rinsed.

The electrochemical reactions can be monitored and controlled by controlling the potential on the electrodes, the amount of current in the reactions, the concentration of the solution, or by time, as is known in the art.

FIGS. 7A, 7B, 7C show nanostructure sensing devices 12-$n$ that each include a counter electrode 20-$n$. In an alternative arrangement, the nanostructure sensing devices 12-$n$ do not include counter electrodes 20-$n$, and a counter electrode 50 is provided in each reactant bath 60, 62, 64. The counter electrodes 50 in each reactant bath 60, 62, 64 can be the same or they can be different.

A pseudo-reference electrode can be used to help control the electrochemical reaction, as is known in the art. Preferably, a pseudo-reference electrode 52 is provided in contact with the reactant baths 60, 62, 64. Alternatively, pseudo-reference electrodes 22-$n$ can be provided within the nanostructure sensing devices, as illustrated above in FIG. 2.

A method of fabricating an electronic system for selectively detecting and identifying a predetermined number of chemical species according to another embodiment of the invention can be understood with reference to FIGS. 7A-7C. Again, the array 10 of nanostructure sensing devices 12-5, 12-6, 12-7 is as shown in FIGS. 7A-7C except that there are no counter electrodes 20-5, 20-6, 20-7, nor pseudo-reference electrodes 22-5, 22-6, 22-7. The array 10 is submerged or partially submerged in the reactant bath 60. A voltage is applied across each pair of contact electrodes 14-5, and a current flows through the nanostructures 18-5. The voltage is increased gradually in each nanostructure sensing device 12-5, thereby gradually increasing current flow through the nanostructures. The increasing energy from the increasing current flow can lead to a reaction between the nanostructures and the reactant, causing formation of one or more point defects. When the point defect forms, there is a large increase in resistance, a sharp decrease in current flow through the nanostructures, and the reaction stops. The characteristic voltage at which the reaction becomes self-limiting, i.e., at which the reaction stops, can be different for each device. In subsequent processing to modify selectivity for sensing of nanostructure sensing devices, it is not necessary to apply an increasing voltage to form the point defects. The previously-found characteristic voltages can be applied for known periods of time until the point defects form and the reaction stops. After modification of nanostructures 18-5, the array 10 is removed from the reactant bath 60, and the array 10 is rinsed.

The array 10 is submerged or partially submerged in the reactant bath 62. A voltage is applied across each pair of contact electrodes 14-6, and a current flows through the nanostructures 18-6. The voltage is increased gradually in each nanostructure sensing device 12-6, thereby gradually increasing current flow through the nanostructures. The increasing energy from the increasing current flow can lead to a reaction between the nanostructures and the reactant, causing formation of one or more point defects. When the point defect forms, there is a large increase in resistance, a sharp decrease in current flow through the nanostructures, and the reaction stops. The characteristic voltage at which the reaction becomes self-limiting, i.e., at which the reaction stops, can be different for each device. In subsequent processing to modify selectivity for sensing of nanostructure sensing devices, it is not necessary to apply an increasing voltage to form the point defects. The previously-found characteristic voltages can be applied for known periods of time until the point defects form and the reaction stops. After modification of nanostructures 18-6, the array 10 is removed from the reactant bath 62, and the array 10 is rinsed.

The array 10 is submerged or partially submerged in the reactant bath 64. A voltage is applied across each pair of contact electrodes 14-7, and a current flows through the nanostructures 18-7. The voltage is increased gradually in each nanostructure sensing device 12-7, thereby gradually increasing current flow through the nanostructures. The increasing energy from the increasing current flow can lead to a reaction between the nanostructures and the reactant, causing formation of one or more point defects. When the point defect forms, there is a large increase in resistance, a sharp decrease in current flow through the nanostructures, and the reaction stops. The characteristic voltage at which the reaction becomes self-limiting, i.e., at which the reaction stops, can be different for each device. In subsequent processing to modify selectivity for sensing of nanostructure sensing devices, it is not necessary to apply an increasing voltage to form the point defects. The previously-found characteristic voltages can be applied for known periods of time until the point defects form and the reaction stops. After modification of nanostructures 18-7, the array 10 is removed from the reactant bath 64, and the array 10 is rinsed.

In any of the embodiments discussed above with reference to FIGS. 7A-7C, the modification reaction can be initiated or controlled by supplying to the array additional forms of energy (not shown), such as ultraviolet radiation, thermal energy, or electrical energy.

Figure 8:
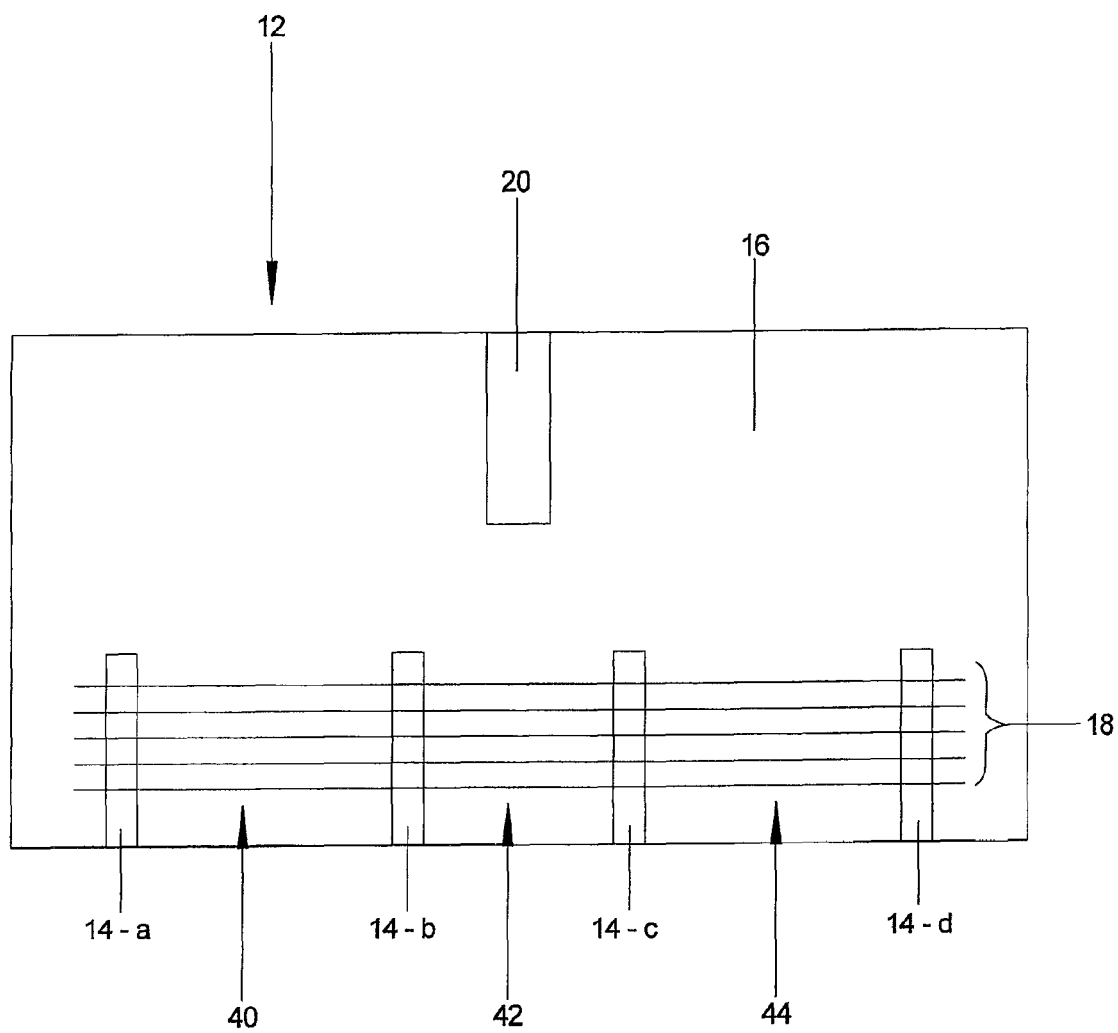
FIG. 8 shows an example of a nanostructure sensing device that has nanostructures spanning across four electrodes.

Although many of the illustrated embodiments show nanostructure sensing devices with only two contact electrodes, any number of contact electrodes can be used, as was described above for FIG. 2. FIG. 8 illustrates a nanostructure sensing device 12 in another arrangement that contains four contact electrodes 14-a, 14-b, 14-c, 14-d on a substrate 16. Nanostructures 18 span across all four contact electrodes 14-a, 14-b, 14-c, 14-d are in electrical contact with the contact electrodes 14-a, 14-b, 14-c, 14-d. Nanostructure section 40 spans the region between contact electrode 14-a and 14-b. Nanostructure section 42 spans the region between contact electrode 14-b and 14-c. Nanostructure section 44 spans the region between contact electrode 14-c and 14-d.

The nanostructures of FIG. 8 can be modified for selectivity for sensing by any of the methods discussed above for FIG. 6 and FIGS. 7A, 7B, 7C. The methods include chemical, electrochemical and self-limiting reactions. Reactants can be provided through chemical jets or in a reactant bath. A counter electrode 20 and a pseudo-reference electrode (not shown) for electrochemical reactions can be supplied in the nanostructure sensing device 12, in the reactant bath or in the chemical jet.

When chemical methods are used for modification of selectivity for sensing, all sections 40, 42, 44 are modified in the same way, unless one or more sections is shielded from the reactant. Alternatively, for electrochemical methods and self-limiting reactions, each section 40, 42, 44 can be modified separately by applying voltages only to electrodes 14-a and 14-b, 14-b and 14-c, respectively. For example, when a first voltage is applied to contact electrodes 14-a and 14-b, and a second voltage, different from the first voltage is applied to counter electrode 20, in the presence of an electrochemical solution, selectivity for sensing for only nanostructure section 40 is modified. If the first voltage is applied to contact electrodes 14-a and 14-c, selectivity for sensing for both nanostructure sections 40 and 42 is modified. As described above, any section 40, 42, 44 can be shielded from the electrochemical solution to prevent modification.

In another example, the device 12 in FIG. 8 is immersed in a liquid or gas reactant. A first voltage is applied to contact electrode 14-b and a second voltage, different from the first voltage, is applied to contact electrode 14-c, and current flows through nanostructure section 42. As both the first and second voltages are increased gradually, current flow through the nanostructure section 42 increases. The increasing energy from the increasing current flow can lead to a reaction between the nanostructure section 42 and the reactant, causing formation of one or more point defects, as discussed above. When the point defect forms, there is a large increase in resistance, a sharp decrease in current flow through the nanostructure section 42, and the reaction stops.

Figure 9A:
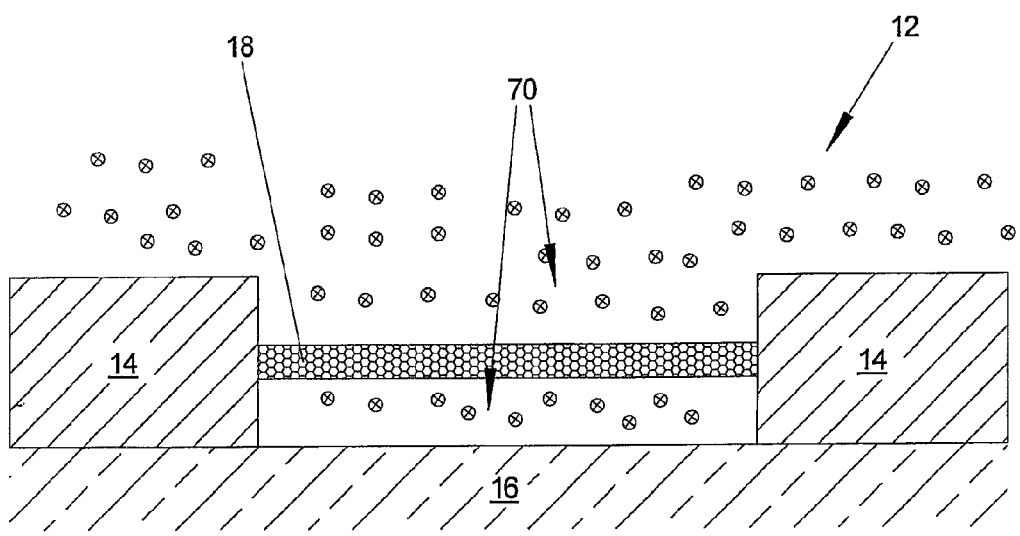
FIG. 9A is a side view of a nanostructure sensing device attached to two contact electrodes and surrounded by a reactant.
Figure 9B:
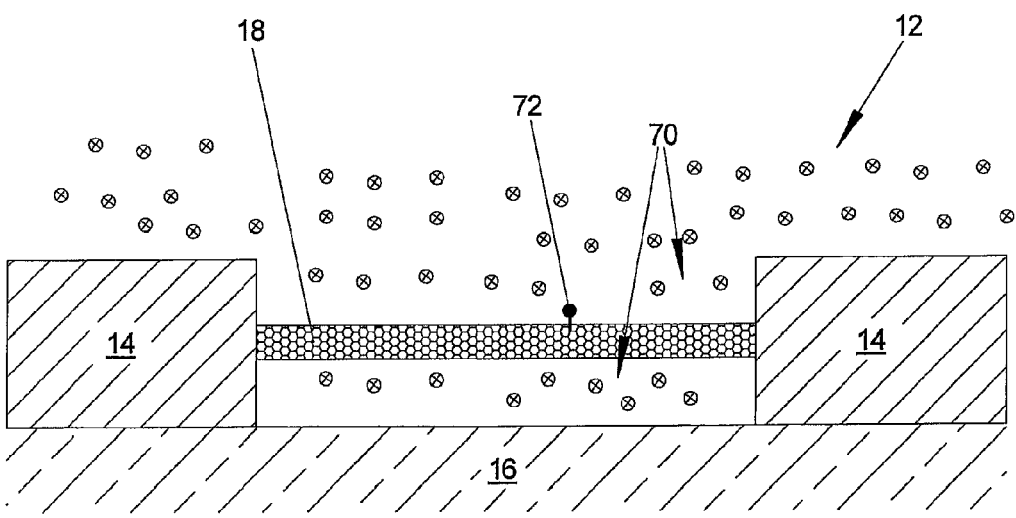
FIG. 9B is a side view of the nanostructure sensing device of FIG. 9A after a voltage has been applied across the two electrodes and a point defect has formed on the nanostructure.
Figure 9C:
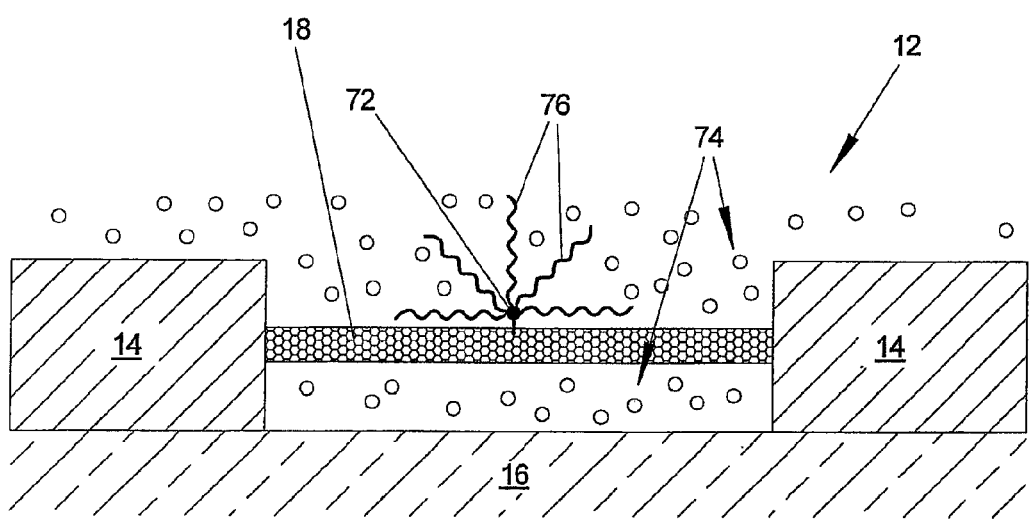
FIG. 9C is a side view of the nanostructure sensing device of FIG. 9B after additional reactants have been applied, and a variety of molecules have attached to form a structure extending from the point defect.

FIGS. 9A, 9B, 9C show a method of modifying selectivity for sensing for a nanostructure in a nanostructure sensing device according to an illustrated embodiment of the invention.

FIG. 9A shows a side view of an individual nanostructure sensing device 12 that includes two contact electrodes 14 on a substrate 16. A nanostructure 18 is suspended above the substrate 16 and is in contact with the two contact electrodes 14, forming a conductive link therebetween. Although only one nanostructure 18 is shown in the illustration of FIG. 9A, any number of nanostructures 18 can make contact with the two contact electrodes 14. The nanostructure 18 is surrounded by reactant molecules 70. The reactant molecules 70 can be in the form of a liquid or a gas. The reactant molecules 70 can be supplied by any of the methods described above or by any other method that will expose the nanostructure 18 to the reactant molecules 70.

In FIG. 9B, a voltage is applied across the contact electrodes 14, causing a current to flow through the nanostructure 18. The voltage is increased gradually, thus gradually increasing the current flow through the nanostructure 18. The increasing energy from the increasing current flow can lead to a reaction between the nanostructure 18 and the reactant molecules 70, causing formation of one or more point defects. At a characteristic voltage a point defect 72 forms, there is a large increase in resistance, a sharp decrease in current flow through the nanostructure 18, and the reaction stops. Thus, a point defect 72 is formed on the surface of the nanostructure 18 by a self-limiting reaction. In other arrangements, more than one point defect 72 can form before the reaction stops. In subsequent processing to modify selectivity for sensing of nanostructure sensing devices, it is not necessary to apply an increasing voltage to form the point defects. The previously-found characteristic voltages can be applied for known periods of time until the point defects form and the reaction stops. In some embodiments, the point defect 72 has a selectivity for sensing chemical species.

FIG. 9C shows a resulting structure extending from the surface of the nanostructure 18 after a few additional steps have been performed. The structure shown in FIG. 9B has been rinsed with another gas or liquid containing reactant molecules 74. The reactant molecules 74 attach to the point defect 72. There can be individual attachments of reactant molecules 74 or a series of attachments of reactant molecules 74, thus forming extended structures 76 from the point defect 72. The attached molecules 74 or the extended structures 76 can have selectivity for sensing chemical species. In other arrangements, reactant molecules 70 are rinsed away by a non-reacting gas or liquid before the nanostructure is exposed to reactant molecules 74.

Although the example illustrated in FIGS. 9A-9C includes only two kinds of reactant molecules 70, 74, a whole series of different reactants can be used to build sensing structures extending from the point defect. It can be desirable to use a series of different reactants to build a sensing structure, for example, when a molecule that can sense the chemical species of interest cannot attach itself to the nanostructure directly. A different molecule can be attached to the nanostructures, and one or more intermediary molecules can be linked, one to the other, to provide a suitable linking site for a sensing molecule.

Figure 10:
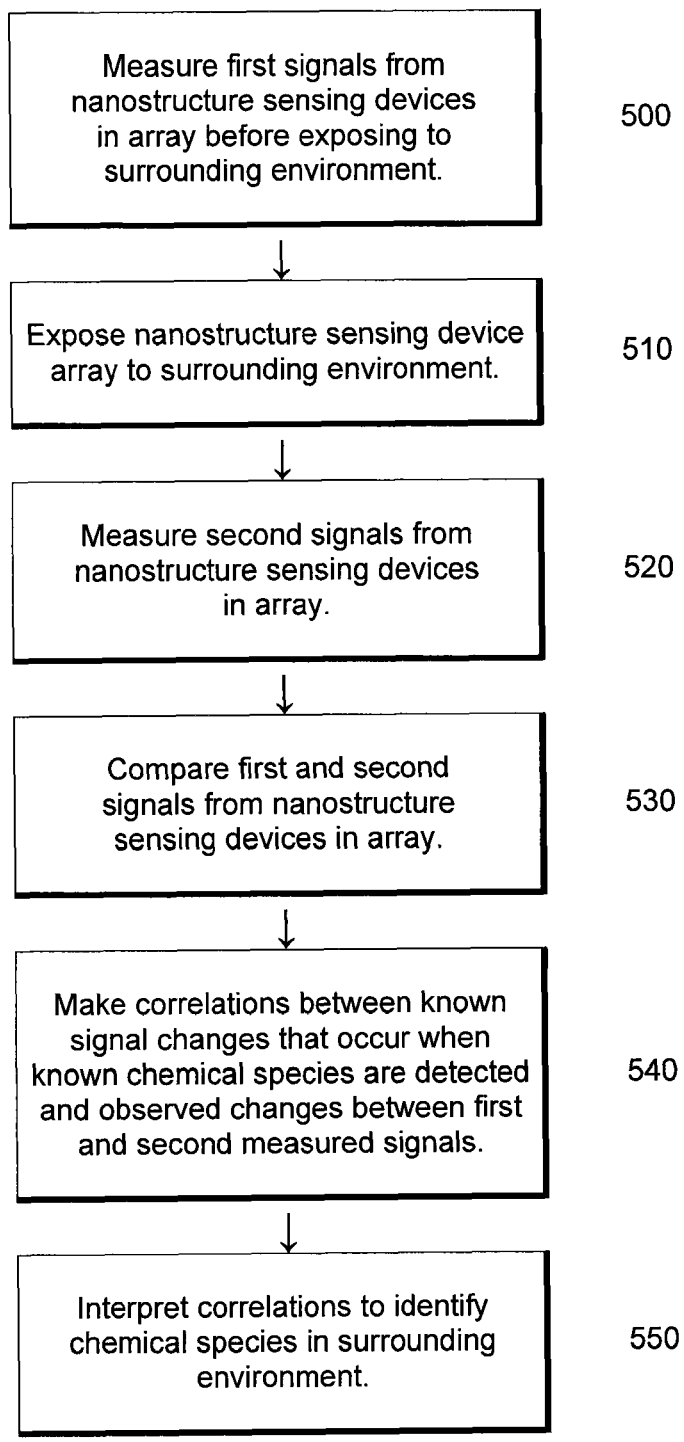
FIG. 10 is a flow chart showing a method for selectively detecting chemical species according to an embodiment of the invention.

FIG. 10 shows a flow chart that summarizes the steps for detecting a plurality of chemical species in a surrounding environment according to an embodiment of the invention. In Step 500, before exposing a sensor array to a surrounding environment of interest, first signals are measured from the nanostructure sensing devices in the array. In Step 510, the sensor array is exposed to the surrounding environment. Second signals are measured from the nanostructure sensing devices in the array in Step 520. In Step 530, the first signals and the second signals from the nanostructure sensing devices in the array are compared. In Step 540, correlations are made between known signal changes that occur when known chemical species are detected and observed changes between the first signal and the second signal from the nanostructure sensing devices in the array. Step 550 involves interpreting the correlations of Step 540 to identify chemical species in the surrounding environment. Signals can include electrical responses, optical responses, thermal responses, and mechanical responses.

In another arrangement, a first gate voltage can be applied to gate electrodes associated with nanostructure sensing devices in at least a first portion of the array before Step 500 and maintained throughout the both the first and second signal measurements. A second gate voltage, different from the first gate voltage, can be applied to gate electrodes associated with nanostructure sensing devices in at least a second portion of the array before Step 500 and maintained throughout the both the first and second signal measurements. In general, different gate voltages can be used for different portions of the array. Gate voltages can be chosen to optimize the response of the nanostructure sensing devices to the chemical species of interest.

In yet another arrangement, within any portion of the array of nanostructure sensing devices a series of different gate voltages can be applied to the gate electrodes associated with each nanostructure sensing device. A series of first and second signal measurements, as described in FIG. 10, are made at each gate voltage, that is, the first and second signals are measured as a function of gate voltage. The differences between measured first and second signals at each gate voltage can be correlated to known differences between first and second signals at each gate voltage when known chemical species are detected. These correlations are used to identify chemical species in the surrounding environment.

Figure 11:
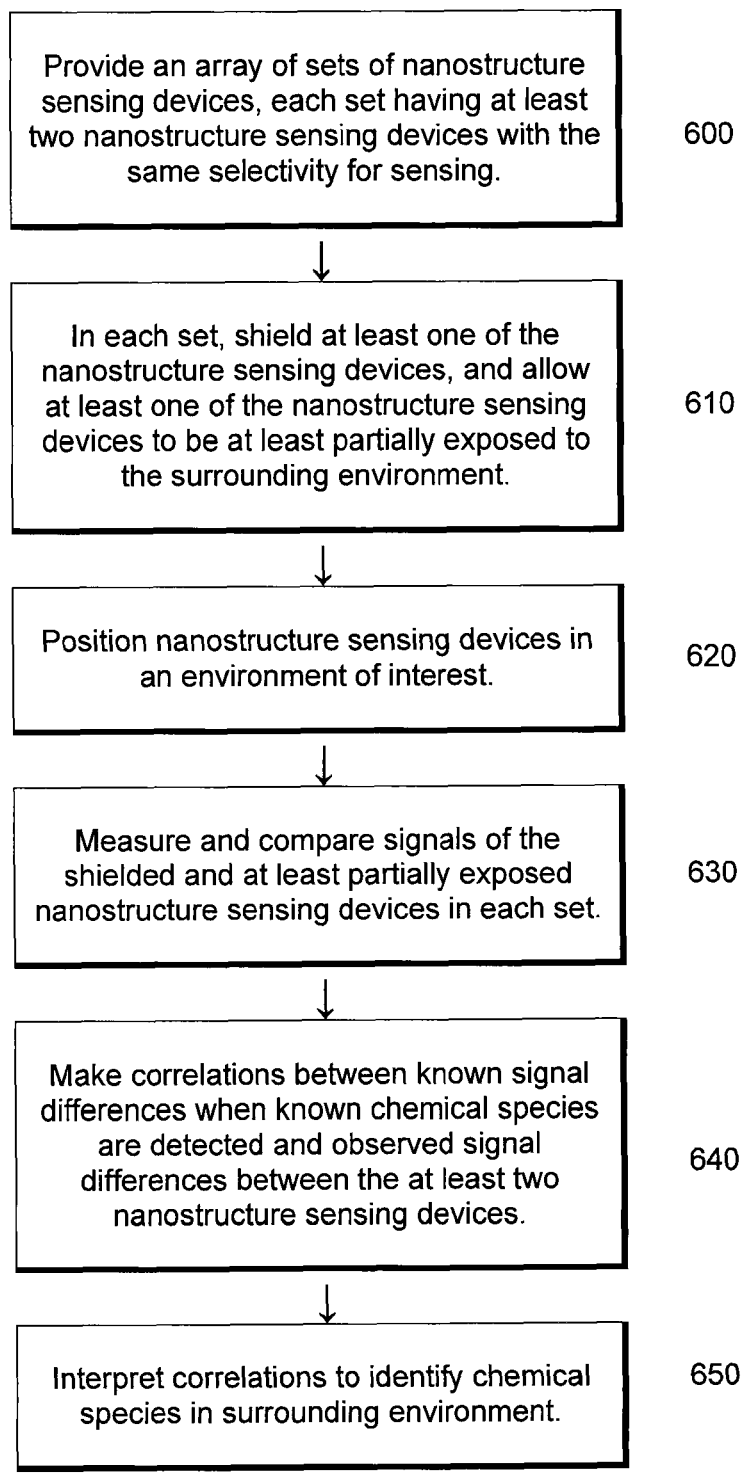
FIG. 11 is a flow chart showing a method for selectively detecting chemical species according to another embodiment of the invention.

FIG. 11 shows a flow chart that summarizes the steps for detecting a plurality of chemical species in a surrounding environment according to another embodiment of the invention. In Step 600, an array of sets of nanostructure sensing devices is provided. Each set has at least two nanostructure sensing devices with the same selectivity for sensing. In Step 610, within each set, at least one of the at least two nanostructure sensing devices is shielded from the surrounding environment, and at least one of the at least nanostructure sensing devices is allowed to be at least partially exposed to the surrounding environment. The nature of the shielding and the at least partial exposure of the nanostructure sensing devices has been discussed in detail above with reference to FIG. 3. In Step 620, the nanostructure sensing devices are positioned in an environment of interest. Signals from both the shielded and at least partially exposed nanostructure sensing devices are measured and compared in Step 630. In Step 640, correlations are made between differences between known signal differences when known chemical species are detected and observed signal differences between the shielded devices and the partially-shielded devices. Step 650 involves interpreting the correlations of Step 640 to identify chemical species in the surrounding environment. Signals can include electrical responses, optical responses, thermal responses, and mechanical responses.

In another arrangement, a first gate voltage can be applied to gate electrodes associated with each of the at least two nanostructure sensing devices in each set in at least a first portion of the array of sets before Step 630 and maintained while measuring and comparing signals from the at least two nanostructure sensing devices in each set. A second gate voltage, different from the first gate voltage, can be applied to gate electrodes associated with each of the at least two nanostructure sensing devices in each set in at least a second portion of the array of sets before Step 630 and maintained while measuring and comparing the signals from the at least two nanostructure sensing devices in each set. In general, different gate voltages can be used for different portions of the array of sets. Gate voltages can be chosen to optimize the response of the nanostructure sensing devices to the chemical species of interest.

In yet another arrangement, a series of different gate voltages can be applied to gate electrodes associated with each of the at least two nanostructure sensing devices in each set in at least a portion of the array of sets and maintained while measuring and comparing the signals from the at least two nanostructure sensing devices in each set at each gate voltage, that is, the signals are measured and compared as a function of gate voltage. Correlations are made between known signal differences at each gate voltage when known chemical species are detected and the measured signal differences at each gate voltage between the at least two nanostructure sensing devices in each set. These correlations are used to identify chemical species in the surrounding environment.

The correlations between measured signals and known signals as described above for FIGS. 10 and 11 can be made through algorithms, such as primary component analysis, which have been developed and used for similar sensing arrays using different sensor technologies. An example of such an algorithm is discussed by Shaffer in U.S. Pat. No. 6,289,328, which is incorporated in its entirety herein by reference.

Areas of application include industrial, medical, agricultural, and environmental monitoring. These can include characterization of water and air for pollutants and biotoxins, both gaseous and liquid chemicals in processing or manufacturing, body fluids (urine, blood, etc.), and breath. For medical applications, the sensors can be used externally on samples or placed in situ for continuous monitoring. As the demand for chemical sensing in military applications, such as for detection of harmful chemical and biological agents, continues to increase, nanostructure sensing device arrays, as described herein are ideally suited to fill this demand. Other applications include sensing simple odors, such as for foodstuffs, drinks, perfumes and essential oils.

This invention has been described herein in considerable detail to provide those skilled in the art with information relevant to apply the novel principles and to construct and use such specialized components as are required. However, it is to be understood that the invention can be carried out by different equipment, materials and systems, and that various modifications, both as to the equipment and operating procedures, can be accomplished without departing from the scope of the invention itself.

We claim:

1. An electronic system for selectively detecting and identifying a plurality of chemical species, comprising an array of nanostructure sensing devices, each nanostructure sensing device comprising at least one nanostructure and having a selectivity for sensing the chemical species, wherein the selectivity of the at least one nanostructure sensing device differs from the selectivity of at least one other nanostructure sensing device, further comprising, in each nanostructure sensing device in the array of nanostructure sensing devices, a contact electrode, and a counter electrode, electrically isolated from the contact electrode.

2. The electronic system of claim 1, wherein the contact electrode is electrically connected to the at least one nanostructure.

3. The electronic system of claim 1, wherein the contact electrode comprises a material selected from the group consisting of aluminum, copper, titanium and tungsten.

4. The electronic system of claim 1, further comprising a protective coating on the contact electrode.

5. The electronic system of claim 4 wherein the protective coating is selected from the group consisting of silicon oxides, metal oxides, polymer films, and nonvolatile organics.

6. The electronic system of claim 1, further comprising a gate electrode in at least a portion of the nanostructure sensing devices in the array of nanostructure sensing devices.

7. The electronic system of claim 1, further comprising a pseudo-reference electrode, electrically isolated from the contact electrode, in at least a portion of the nanostructure sensing devices in the array of nanostructure sensing devices.

8. The electronic system of claim 1, wherein the nanostructure sensing devices comprise at least one nanostructure selected from the group consisting of single-walled nanotubes, multi-walled nanotubes, nanofibers, nanowires, nanocoils, nanospheres, nanocages, nanococoons, nanohorns, nanoropes, nanotori, nanorods, nanoplatelets, and other extended molecules such as polymers, dendrimers, organometallics, fullerene-like molecules, and combinations thereof.

9. The electronic system of claim 1, wherein the nanostructure sensing devices comprise at least one nanostructure comprising an approximately linear form.

10. The electronic system of claim 1, wherein the nanostructure sensing devices comprising at least one nanostructure comprises elements selected from the group consisting of boron, carbon, combinations thereof, and combinations with nitrogen.

11. The electronic system of claim 1, further comprising at least two nanostructure sensing devices having the same selectivity for sensing, wherein at least one of the at least two nanostructure sensing devices is impermeably shielded from at least the plurality of chemical species, and at least one of the at least two nanostructure sensing devices is at least partially exposed to at least the plurality of chemical species.

12. The electronic system of claim 1, wherein the counter electrode is configured to at least in part modify the selectivity of the nanostructure sensing device.

* * * * *